US006991934B2

(12) United States Patent
Walton et al.

(10) Patent No.: US 6,991,934 B2
(45) Date of Patent: Jan. 31, 2006

(54) TISSUE PROCESSOR WITH INTEGRATED VALVE

(75) Inventors: George Alan Walton, Tarporley (GB); Christopher James Leighton, Elton (GB)

(73) Assignee: Thermo Shandon Limited, Cheshire (GB)

( * ) Notice: Subject to any disclaimer, the term of this patent is extended or adjusted under 35 U.S.C. 154(b) by 388 days.

(21) Appl. No.: 10/251,123

(22) Filed: Sep. 20, 2002

(65) Prior Publication Data

US 2003/0059928 A1 Mar. 27, 2003

(30) Foreign Application Priority Data

Sep. 21, 2001 (GB) .................................... 0122801

(51) Int. Cl.
*C12M 1/02* (2006.01)
(52) U.S. Cl. ................ 435/307.1; 435/286.5; 422/102; 366/276; 137/625.41; 118/429
(58) Field of Classification Search ............ 435/284.1, 435/302.1, 303.3, 307.1, 286.5, 286.7; 422/99, 422/102, 103; 137/625.15, 625.11, 625.21, 137/625.46, 625.41; 118/429; 366/276–278
See application file for complete search history.

(56) References Cited

U.S. PATENT DOCUMENTS 2,959,151 A * 11/1960 Ehrlich ....................... 118/429
3,238,971 A * 3/1966 Cerone .................. 137/614.11
4,099,483 A 7/1978 Henderson
4,199,558 A 4/1980 Henderson
4,604,964 A 8/1986 Gordon
4,834,019 A 5/1989 Gordon

FOREIGN PATENT DOCUMENTS

GB 1 536 422 12/1978

* cited by examiner

*Primary Examiner*—William H. Beisner
(74) *Attorney, Agent, or Firm*—Fulwider Patton LLP (57) ABSTRACT

A tissue processor is disclosed for processing biological tissue, for example, for mounting on microscope slides. The tissue processor has a valve arrangement in the bottom of a tissue processing chamber, whereby a selected one of a plurality of fluid ports formed in a base of the tissue processing chamber may be connected with the interior of the chamber for supply of processing fluid thereto or discharge of fluid from the chamber. In this way different processing fluids may be passed into and removed from the processing chamber in succession, for processing of tissue samples contained in baskets within the chamber. The valve arrangement comprises a rotary disc at the bottom of the chamber and in sealing engagement with a valve surface on the base of said chamber, the valve surface being provided with a plurality of ports connected with respective said fluid inlets. The rotary disc is provided with a single port therethrough so that by rotating the disc into a selected position the port in the rotary disc can be brought into register with a selected one of the plurality of fluid ports formed in the base of the tissue processing chamber.

1 Claim, 7 Drawing Sheets

TISSUE PROCESSOR WITH INTEGRATED VALVE

THIS INVENTION relates to tissue processors for processing biological tissue, for example, for mounting on microscope slides.

Processors of the type referred to are intended for use in subjecting tissue samples to a sequence of processing steps, involving treatment of the sample in various treatment fluids in succession. It is an object of the invention to provide a tissue processor which will facilitate such treatments.

According to the invention, there is provided a tissue processor comprising a vessel having an interior chamber in communication with a valve arrangement whereby a selected one of a plurality of fluid inlets may be connected with the interior of the chamber for supply of processing fluid thereto and/or whereby the chamber may alternatively be connected with a discharge outlet, or a selected one of a plurality of discharge outlets, for discharge of fluid from the processor chamber, characterised in that the valve arrangement comprises a rotary member in sealing engagement with a valve surface fixed with respect to said chamber, said valve surface being provided with a plurality of ports connected with or providing respective said fluid inlets, and said rotary member being provided with a port selectively communicable with a said inlet and having an opening into a said chamber and communicating via a duct or passage with the last-mentioned said port.

In a preferred embodiment, the processor chamber has a base in which said inlets are arranged in a ring centered on a rotary axis of said rotary member, and are selectively connectable with a single said port in an opposing part of said rotary member, the latter being formed as a disc centered on said axis and rotatable about said axis, sealing means being provided to effect a seal between the rotary member and said base around the aligned registering ports of the rotary member and said base and said axis.

An embodiment of the invention is described below with reference to the accompanying drawings, in which.

Referring to the drawings, a tissue processor comprises a vessel 10 which is generally cylindrical about a vertical axis, having a generally horizontal circular base wall 12, and an upstanding cylindrical side wall 14 centred on said axis and terminating in a rim defining an opening in a top panel 16.

Figure 1:
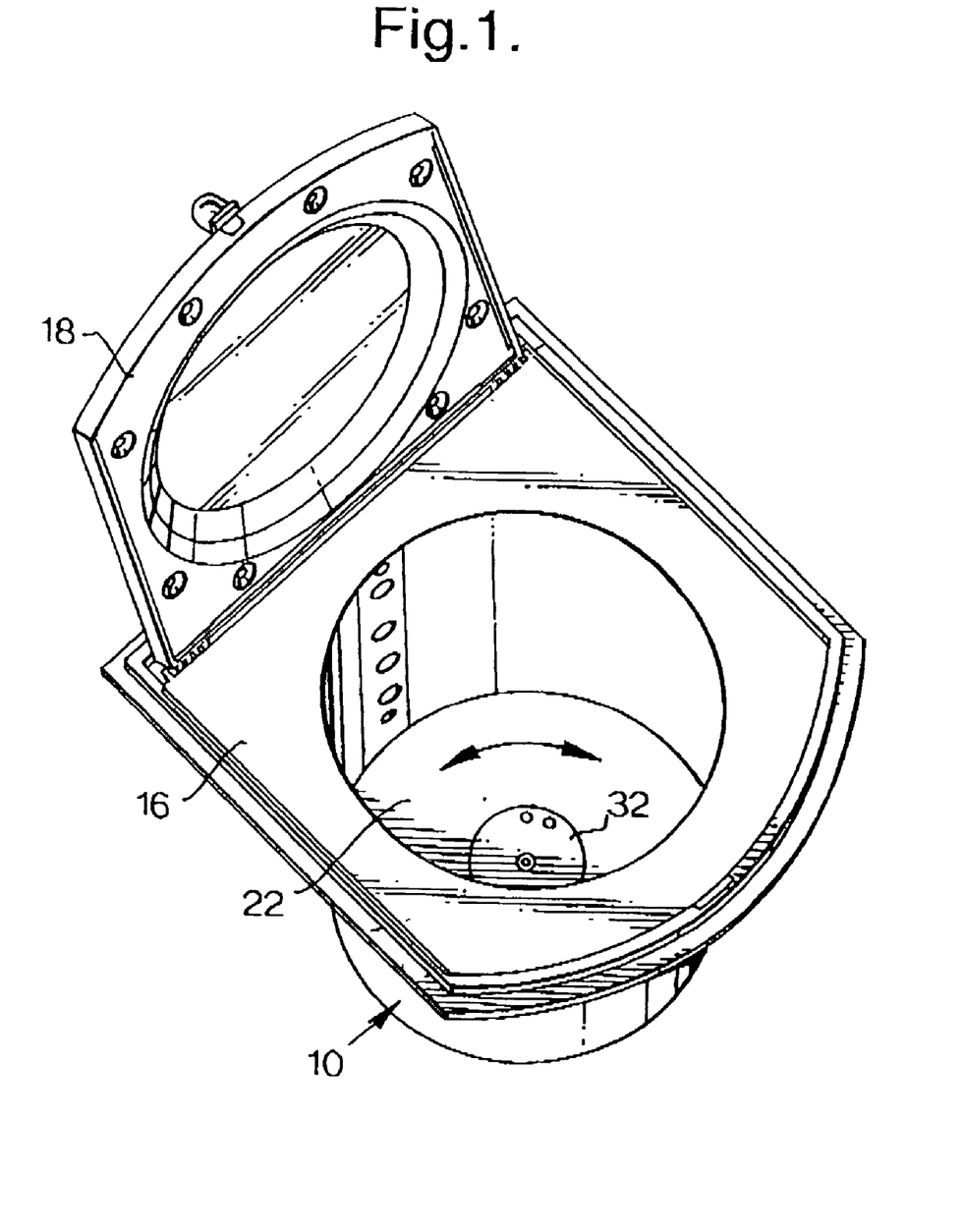
FIG. 1 is a perspective view from above of part of a tissue processor in accordance with the invention.

A lid 18, pivotally connected to the top panel 16, closes the upper end of the processor chamber in the closed lowered position of the lid (shown in FIGS. 3 and 4) and allows access to the interior of the processor chamber in the raised position of the lid, as shown in FIG. 1.

Figure 6:
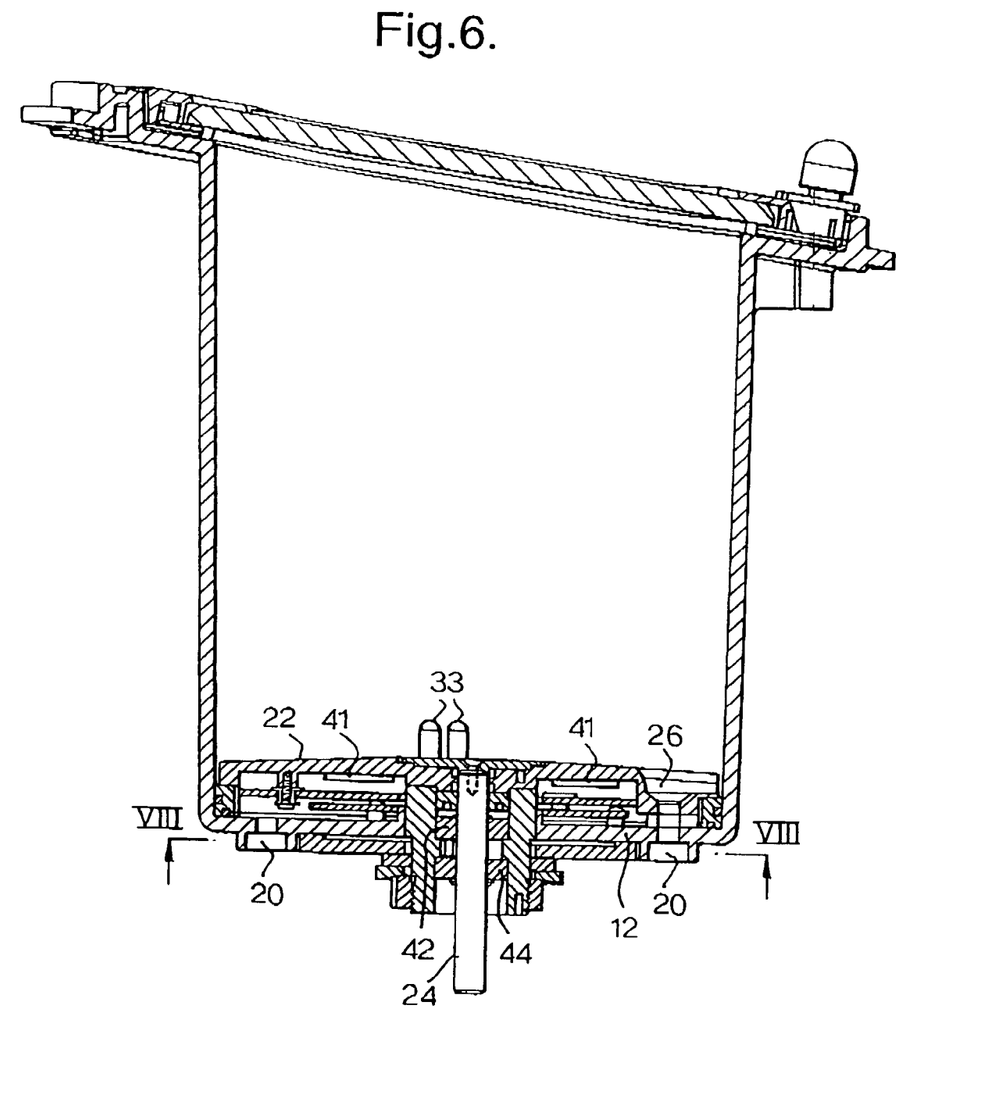
FIG. 6 is a vertical section view similar to FIG. 3, but taken along a plane at an angle with respect to the plane of FIG. 3 and showing additional elements.
Figure 7:
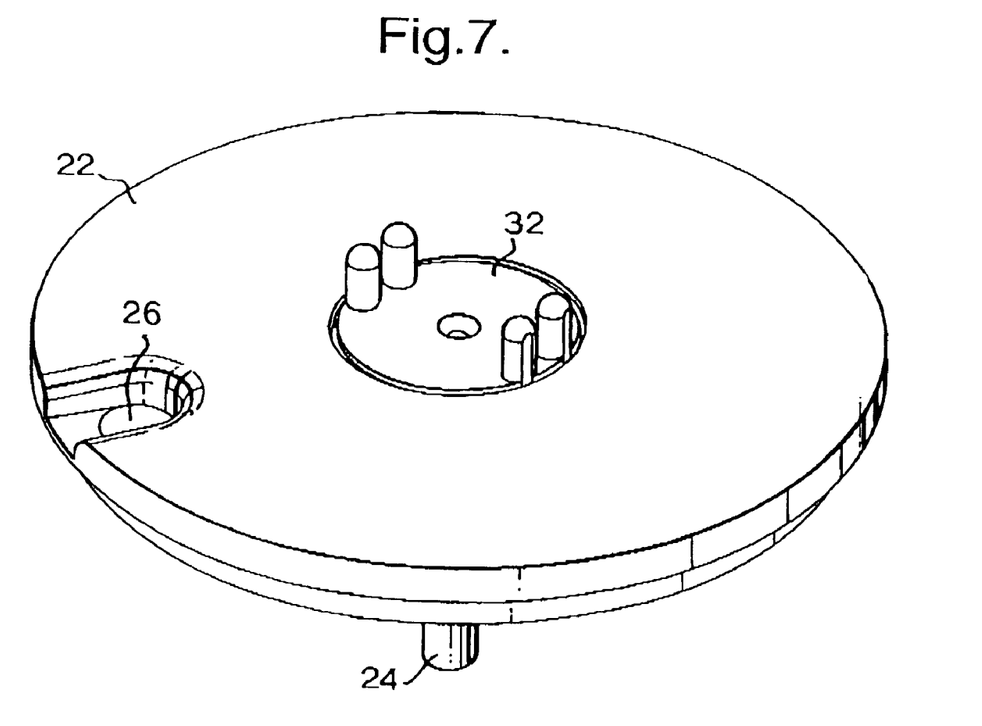
FIG. 7 is a perspective view of a detail.

A plurality of ports 20 (see FIG. 2), are formed through the base wall 12, arranged in a circle centred on the central axis of the processor chamber, these ports thus being spaced apart angularly about this central axis. The plane of FIG. 6 is selected to show one of the ports 20 in section.

Within the processor chamber, just above the circular base of the latter, is a generally flat rotary valve disc 22 which is secured to the upper end of a hollow shaft 40 extending vertically through a central axial bore through the base 12. The disc member 22 is preferably of corrosion resistant metal, e.g. stainless steel. The shaft 40 is coaxial with vessel 10 and is rotatable with respect to the vessel 10 about the central vertical axis of the vessel. The disc 22 has adjacent its periphery a single opening or port 26 (FIG. 4) which can be placed in communication with a respective one of the ports 20, (as shown in FIG. 6), by rotating the disc 22 to the appropriate angular position, about its axis, in which said port 26 in the disc 22 is in precise and sealing registry with the respective port 20 in base 12.

Disc 22 is secured (by means not shown) to the upper end of a hollow shaft 40 which is rotatable within a central axial bore in base 12. The hollow shaft 40 projects below the base 12 of the container 10, and passes through an aligned central aperture in a cover plate 31 fixed under the base 12. The lower end of the shaft 40 is externally screw-threaded and carries a nut 35 screw-threadedly engaged on the shaft 40. A washer 36 and a bearing member 38 are located around shaft 40 between nut 35 and the cover plate 31.

A sealing ring 28 of elastomeric material, carried by the disc 22 on the underside of the latter, encircles port 26 and closely engages the upper surface of the base 12 to prevent leakage of treatment fluid into the space below disc 22 via the port 26 or via a port 20 which is aligned with port 26, during supply of such fluid to the vessel 10 by way of the aligned ports 20, 26 or discharge of such fluid from the vessel by way of the aligned ports 20,26.

In use of the apparatus, the ports 20 are connected (by means not shown) to respective reservoirs, (not shown) of respective treatment fluids, each reservoir having associated pumping means (not shown) whereby, when the port 26 is in alignment with the respective port 20, the respective fluid may be pumped from its respective reservoir to the vessel 10 or from the vessel 10 into its respective reservoir.

Figure 2:
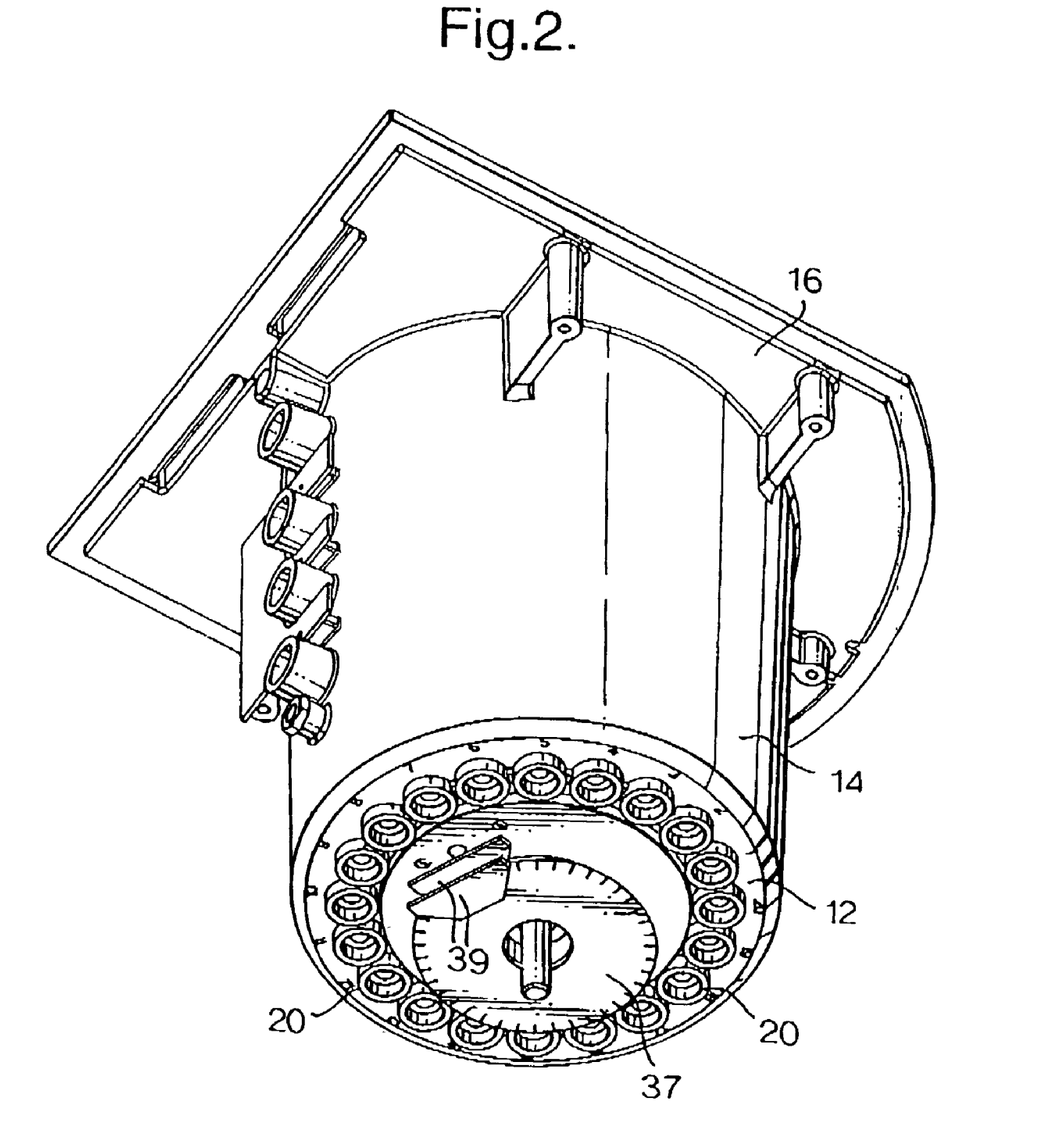
FIG. 2 is an underneath perspective view of the tissue processor part of FIG. 1.

Hollow shaft 40 serves principally to rotate the disc 22 and to provide a tension force producing controlled biasing of the disc 22 towards the base 12. As best shown in FIG. 2, the lower end of the shaft 40 may carry an encoded disc 37 co-operating with sensors (not shown) carried by members 39 carried in turn by cover plate 31, for monitoring of the rotational position of the disc 22.

Drive for rotation of the disc 22 is applied, eg. by a geared electric motor, (not shown), to a shaft 24 which extends coaxially within shaft 40 and is rotationally supported within the shaft 40 by bearings 42 and 44. Shaft 24 is provided with drive features which move within corresponding features in hollow shaft 40, (see FIG. 8), such that angular agitation or oscillation of the shaft 24 about its axis can be provided over a significant arc without moving the disc 22. Driving shaft 24 until these drive features engage allows movement of the disc 22, (see below).

Figure 8:
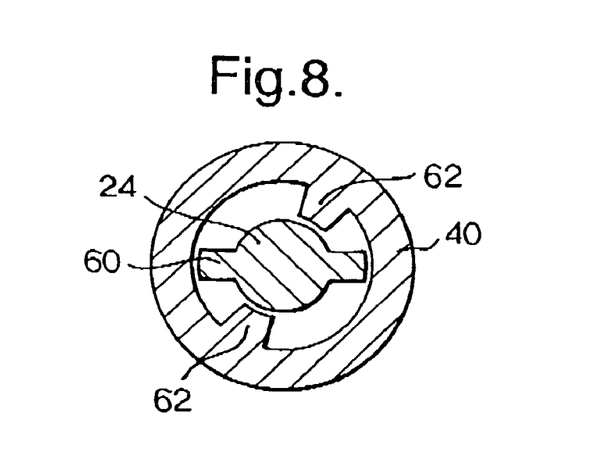
FIG. 8 is a diagrammatic section view of a further detail.

Shaft 24 has fixed at its upper end an agitator 32 received in a central recess in the upper surface of disc 22. The shaft 24 and agitator 32 are rotatable in disc 22 and are sealed with respect thereto. The shaft 24 is further sealed with respect to shaft 40 by a seal 46 adjacent the upper end of shaft 40. The agitator 32 comprises a flat disc received within said central recess and prongs 33 projecting upwardly from the upper surface of said flat disc, above the upper surface of the disc 22. As illustrated in FIG. 8, which is a fragmentary view in horizontal section along the line VIII—VIII in FIG. 6, said drive features on the shaft 24 preferably comprise, at an intermediate position along the length of the shaft 24, lateral projections or teeth 60 which can engage with complementary teeth 62 provided at an intermediate position along the length of hollow shaft 40, these teeth 62 forming the corresponding features in shaft 40 referred to above. The teeth 62 project inwardly from the internal surface of the shaft 40. As will be understood from FIG. 8, starting from one position relative to shaft 40 in which the flanks of the teeth 60 of shaft 24 are engaged with flanks of the teeth 62 of shaft 40, the shaft 24 is able to make a substantial movement about its central axis through an arc, for example 140 degrees, in the sense required to separate the last-mentioned flanks of the teeth 60 from the last mentioned flanks of the teeth 62 before the other flank of each tooth 60 engages the other flank of the other tooth 62 of shaft 40. Whilst in the arrangement shown there are two diametrically opposed teeth on shaft 24 and to two diametrically opposed teeth on shaft 40, each shaft 24,40 may have only one such tooth allowing oscillation through a larger arc or may have more than two equally spaced teeth allowing oscillation through only a smaller arc.

Accordingly it is possible to impart rotary oscillation to shaft 24, with an amplitude up to the extent of said arc, without moving the shaft 40 or disc 22. Such oscillatory movement is used to agitate the specimens in a basket, (not shown) in the vessel to ensure thorough contact of the specimens with the treatment fluid in the processor chamber. Thus the prongs 33 engage such basket so that the basket, and the specimens carried by the basket, are moved through the treatment liquid rather than the treatment liquid being moved through the basket, past the specimens.

However, by moving the shaft 24 through a greater angular range, greater than the extent of said arc, the "lost motion" between the shaft 24 and the shaft 40 is taken up and the shaft 40 and with it the disc 22 can be rotated to a fresh position, thus disconnecting the port 26 from the port 20 to which it was previously connected and connecting it to a different port for supply of a different treatment fluid. The treatment fluid is withdrawn into the source from whence it came at the end of the treatment step with that fluid.

As indicated above, the disc 22 may be rotated in a controlled manner via shaft 40, rotated in turn by shaft 24, to place the port 26 into communication with a selected port 20. There is sufficient distance between adjoining ports 20 to allow the port 26 and the aligned opening in the elastomeric seal 28 to be entirely occluded by the base 12 so that liquid cannot enter or leave the chamber. Thus the disc 22 need make only a small rotational movement to change from a position in which a port 20 is in full communication with the interior of the chamber and a position in which the chamber is sealed off from any such port 20.

For sealing of the interior of the vessel 10 with respect to the disc 22, a rectangular-section sealing ring 30 is located in a circumferential rebate around the periphery of the disc 22 at the lower edge of the latter, the ring 30 being sealed with respect to the wall 14 of the vessel by a first O-ring accommodated in a peripheral groove in the sealing ring 30 and the sealing ring 30 being further sealed with respect to the base 12 of the vessel by a further O-ring accommodated in an annular groove in the lower end face of the sealing ring 30. In operation of the apparatus, the sealing ring 30 remains stationary within the vessel and co-operates sealingly with the under-surface of the rim of the valve disc 22 and thus allows rotation of the valve disc 22 relative to the container whilst preventing passage of treatment fluid between the ring 30 and the rim of the sealing disc 22. The ring 30 is of PTFE or like material and provides an adequate seal with respect to the polished underside of the rim of the valve disc 22. The material of the ring 30 is chosen for its good wear and low friction properties. The elastomeric O-rings in ring 30 take up irregularities in the fit of the ring 30 with respect to the vessel 10. The friction of the O-rings with respect to the vessel wall and base and with respect to the ring 30 is sufficient to ensure that the ring 30 will remain stationery whilst the disc 22 rotates upon it.

In use of the apparatus, the fluid within the vessel may at any time be agitated or stirred to ensure circulation of the fluid around the samples contained therein, by limited rotation of the shaft 24. The shaft 40 may not need to be sealed with respect to base 12 because the sealing ring 30 and the port seal 28 acting between disc 22 and base 12 prevents fluid from reaching the bore in base 12 which receives shaft 40. However, for further assurance of sealing, the shaft 40 may be sealed with respect to the base, e.g. by means of an "O" ring (not shown) around the shaft 40.

Figure 3:
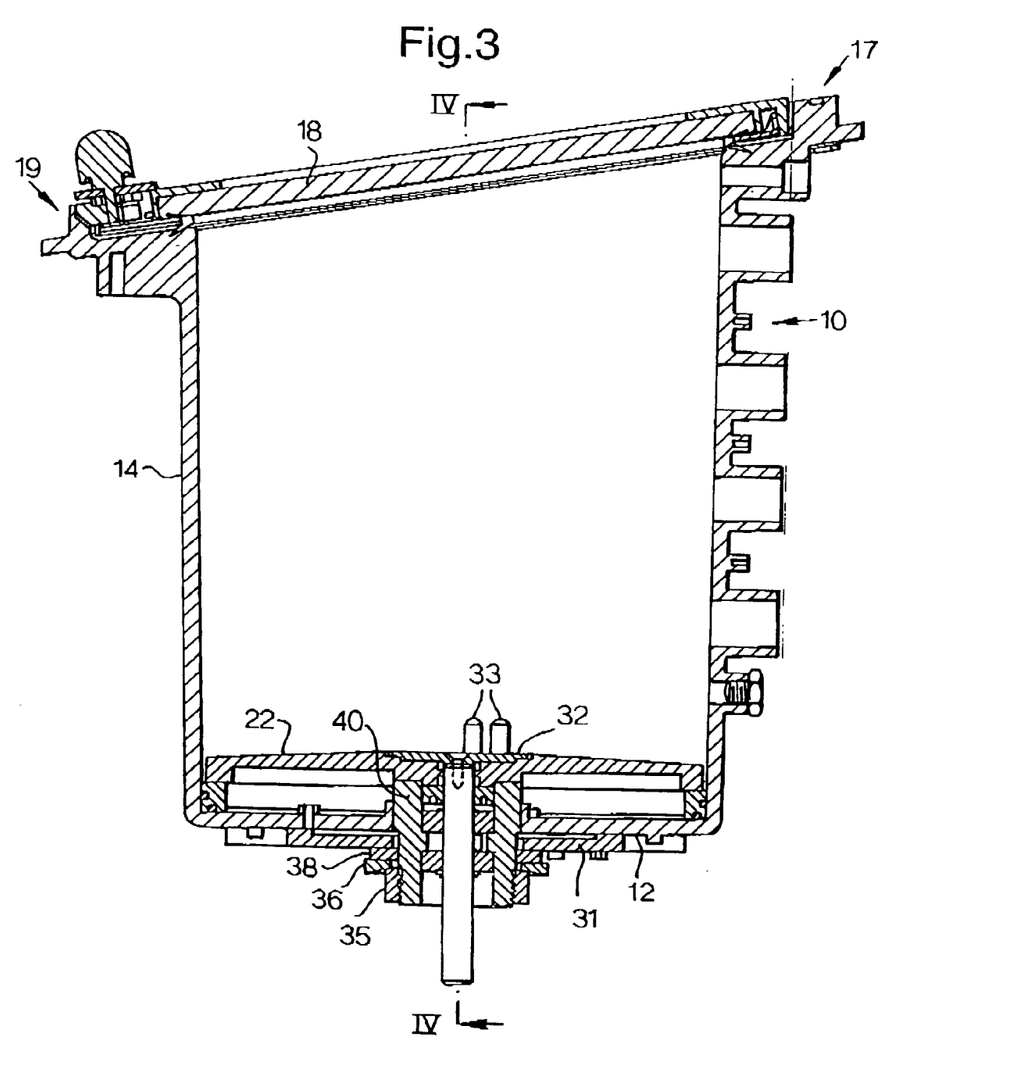
FIG. 3 is a vertical axial section view of said part of the tissue processor with some components omitted for clarity.
Figure 4:
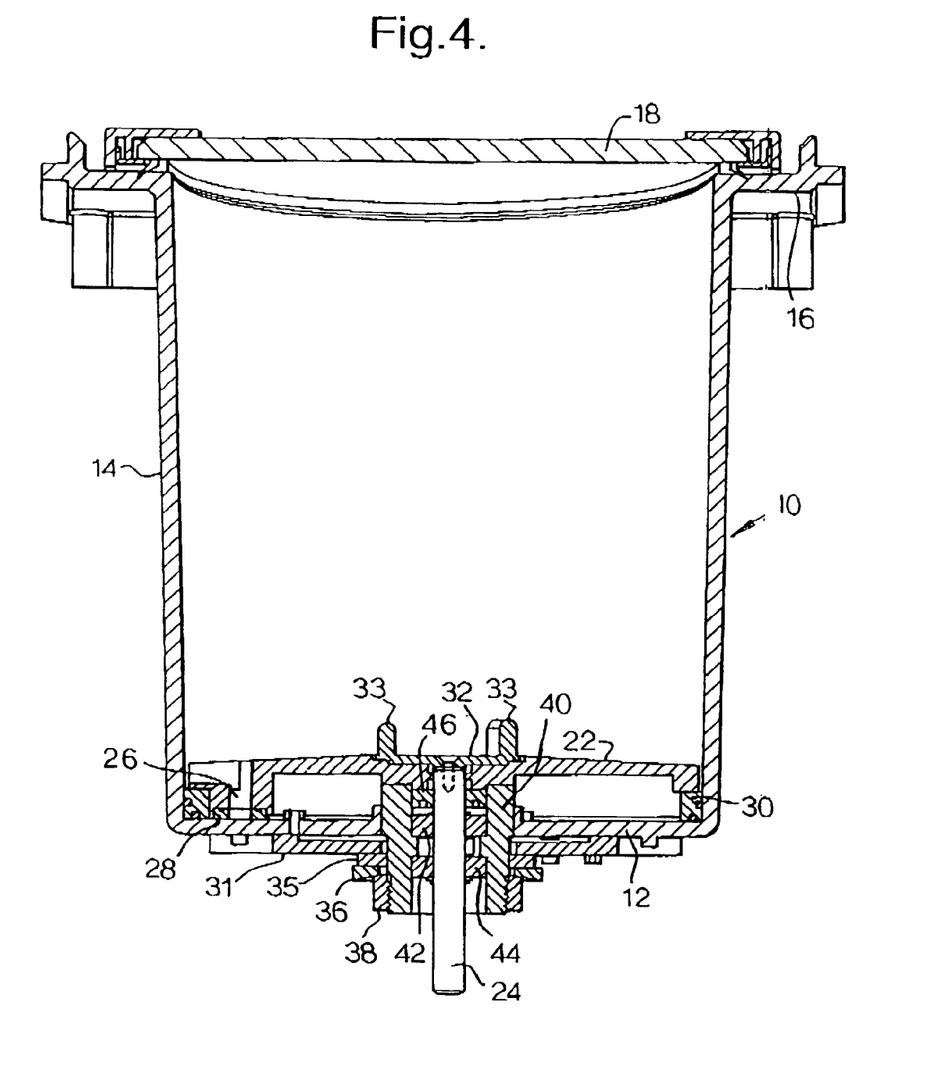
FIG. 4 is vertical axial section view along the line IV—IV in FIG. 3.
Figure 5:
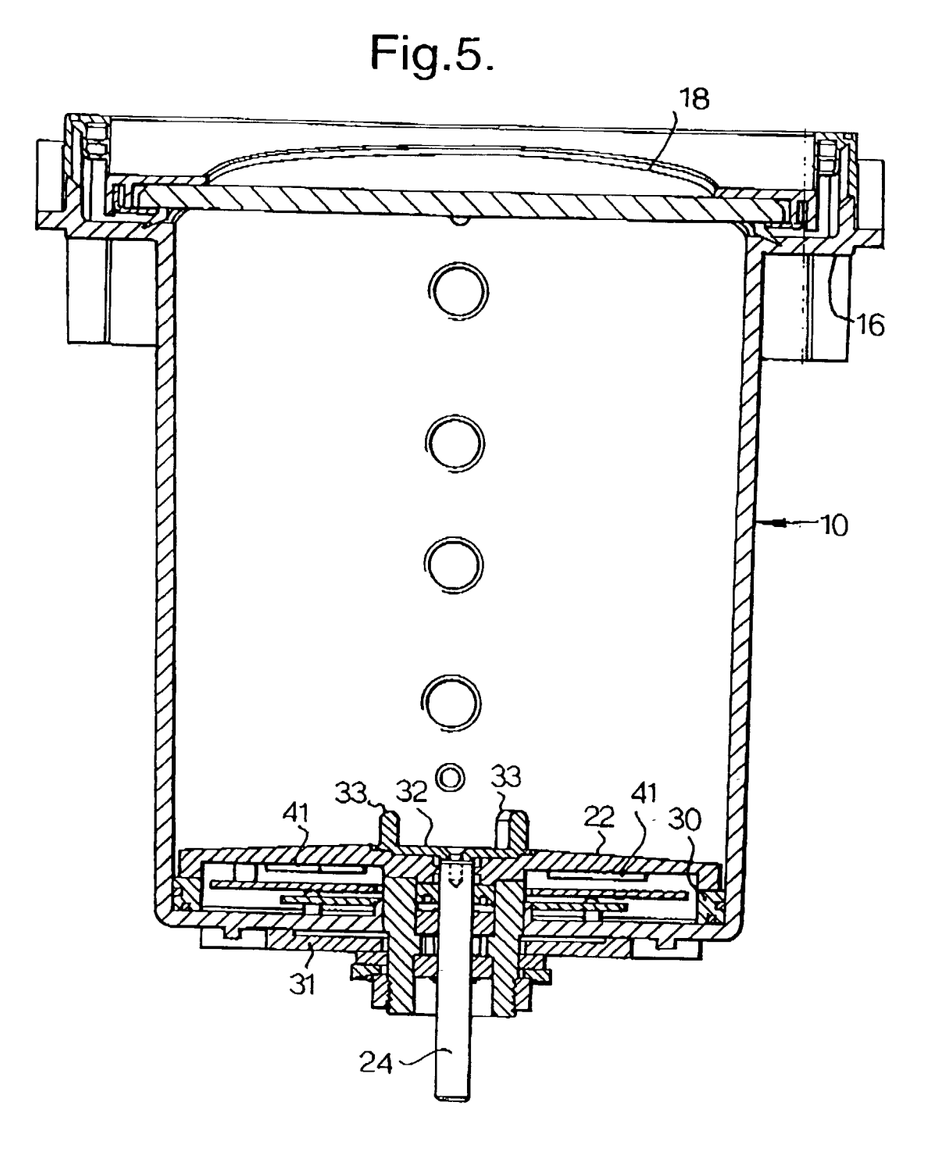
FIG. 5 is a vertical section view in the same plane as FIG. 4, but looking in the opposite direction.

The view which forms FIG. 3 shows several openings into the processor vessel at the back of the latter, arranged in a vertical row. These are holes for an air connection, a thermistor and level sensors, (not shown).

The fluid in the processor chamber may be heated by means of a conformal electrical heating element 41 applied to the underside of the rotary valve disc 22 and supplied with electrical current via slip-rings which may be carried on a printed circuit board (not shown) mounted on the underside of disc 22, these slip rings being engaged by electrical contacts or brushes (not shown) mounted on a plate (not shown) fixed to the vessel 10 and connected to a source of electrical current via conductors extending sealingly through the base 12 of vessel 10.

In the processor according to the invention, the fact that each treatment fluid can enter and leave the treatment chamber by its own port in the base 12 significantly reduces cross-contamination of treatment fluids.

In the preferred embodiment, the vessel 10 is moulded from a chemically resistant polymer. As compared with a pressed metal vessel, this makes it possible to incorporate detailed features, such as the individual ports, with tubular extensions, etc., to a much greater degree. Furthermore, the polymer construction affords better heat insulation than a metal vessel.

What is claimed is:

1. A tissue processor comprising a vessel having an interior chamber in communication with a valve arrangement whereby a selected one of a plurality of fluid inlets may be connected with the interior of the chamber for supply of processing fluid thereto and/or whereby the chamber may alternatively be connected with a discharge outlet, or a selected one of a plurality of discharge outlets, for discharge of fluid from the processor chamber, the valve arrangement including a rotary member in sealing engagement with a valve surface fixed with respect to said chamber, said valve surface being provided with a plurality of ports connected with or providing respective said fluid inlets, and said rotary member being provided with a port selectively communicable with one of said inlets and having an opening into a said chamber and communicating via a duct or passage with the last-mentioned said port, said valve arrangement including a lost motion arrangement comprising a driving shaft coaxial with said rotary member and rotatable with respect to the rotary member through a limited angle, first abutment means fixed with respect to said rotary member and second abutment means carried by said driving shaft, such that the driving shaft can rotate through said limited angle relative to the rotary member between a first limiting position in which the abutment means carried by the driving shaft abuts said abutment means fixed with respect to the rotary member and a second limiting position in which the abutment means carried by the driving shaft abuts said abutment means fixed with respect to the rotary member, wherein the processor chamber has a base in which said inlets are arranged in a ring centered on a rotary axis of said rotary member, and said inlets are selectively connectable with a single said port in an opposing part of said rotary member, the latter being formed as a disc centered on said axis and rotatable about said axis, sealing elements being provided to effect a seal between the rotary member and said base around the aligned registering ports of the rotary member and said base and said axis, and wherein said coaxial driving shaft is further connected to an agitator which is rotatable, about said rotary axis, within said chamber, relative to said base and relative to said rotary member, whereby by moving the driving shaft with a rotationally oscillatory motion relative to said base, through limited angles defined by said lost motion arrangement, said agitator can be oscillated within said vessel without moving the disc and whereby by moving the driving shaft through a greater angular range the rotary member can be rotated, via said driving shaft, about said axis from a position in which said port in the rotary member is in communication with one of said ports in said chamber base to a position in which said port in the rotary member is in communication with a different one of said ports in said chamber base.

* * * * *